United States Patent [19]

Pees

[11] Patent Number: 5,756,509

[45] Date of Patent: May 26, 1998

[54] TRIAZOLOPYRIMIDINE DERIVATIVES

[75] Inventor: Klaus-Jürgen Pees, Mainz, Germany

[73] Assignee: Shell Research Limited, Waterloo, United Kingdom

[21] Appl. No.: 838,013

[22] Filed: Apr. 22, 1997

Related U.S. Application Data

[63] Continuation of Ser. No. 458,009, Jun. 1, 1995, abandoned, which is a continuation of Ser. No. 205,000, Mar. 3, 1994, abandoned.

[30] Foreign Application Priority Data

Mar. 4, 1993 [EP] European Pat. Off. .............. 93103465

[51] Int. Cl.$^6$ .................... C07D 487/04; A01N 43/50
[52] U.S. Cl. .............................. 514/258; 544/263
[58] Field of Search .................. 544/263; 514/258

[56] References Cited

U.S. PATENT DOCUMENTS

| | | | |
|---|---|---|---|
| 4,036,840 | 7/1977 | O'Brien et al. | 546/263 |
| 4,189,483 | 2/1980 | Snowling | 514/258 |
| 4,199,584 | 4/1980 | Cox et al. | 514/258 |
| 4,567,263 | 1/1986 | Eicken et al. | 544/263 |
| 4,617,303 | 10/1986 | Eicken et al. | 544/263 |

FOREIGN PATENT DOCUMENTS

| | | | |
|---|---|---|---|
| 550113 A3 | 7/1993 | European Pat. Off. | 544/263 |
| 569734 | 11/1975 | Switzerland . | |

OTHER PUBLICATIONS

Tenor et al. Chem Abstr. vol. 70 No. 11 Abstract No. 47491 (1968).

*Primary Examiner*—Donald G. Daus
*Attorney, Agent, or Firm*—Joseph M. Mazzarese

[57] ABSTRACT

This invention relates to certain triazolopyrimidine derivatives of the general formula

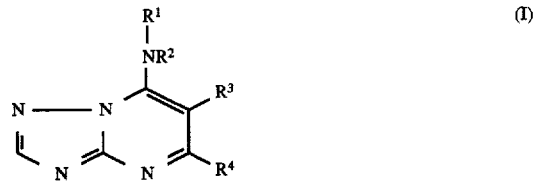

(I)

in which $R^1$ represents an optionally substituted alkyl, alkenyl, alkynyl, alkadienyl, cycloalkyl, bicycloalkyl or heterocyclyl group; $R^2$ represents a hydrogen atom or an alkyl group; or $R^1$ and $R^2$ together with the interjacent nitrogen atom represent an optionally substituted cycloalkyl or heterocyclic ring; $R^3$ represents an optionally substituted cycloalkyl or heterocyclyl group; and $R^4$ represents a hydrogen or halogen atom or a group —$NR^5R^6$ where $R^5$ represents a hydrogen atom or an amino, alkyl, cycloalkyl or bicycloalkyl group and $R^6$ represents a hydrogen atom or an alkyl group; processes for their preparation; compositions containing such compounds and their use as fungicides.

16 Claims, No Drawings

TRIAZOLOPYRIMIDINE DERIVATIVES

This application is a continuation, of application Ser. No. 08/458,009, filed Jun. 1, 1995, which is a continuation of Ser. No. 08/205,000, filed Mar. 3, 1994, both now abandoned.

This invention relates to certain triazolopyrimidine derivatives, a process for their preparation, compositions containing such compounds and their use as fungicides.

European application no. 92204097.7 discloses compounds of the general formula

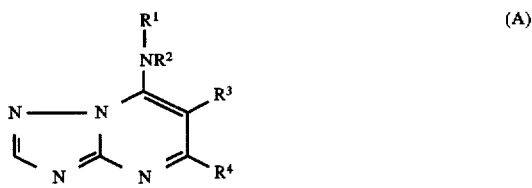
(A)

in which $R^1$ represents an optionally substituted alkyl, alkenyl, alkynyl, alkadienyl, cycloalkyl, bicycloalkyl or heterocyclyl group; $R^2$ represents a hydrogen atom or an alkyl group; or $R^1$ and $R^2$ together with the interjacent nitrogen atom represent an optionally substituted heterocyclic ring; $R^3$ represents an optionally substituted aryl group; and $R^4$ represents a hydrogen or halogen atom or a group —$NR^5R^6$ where $R^5$ represents a hydrogen atom or an amino, alkyl, cycloalkyl or bicycloalkyl group and $R^6$ represents a hydrogen atom or an alkyl group. These compounds are fungicidally active, especially against fungi which are members of the ascomycete class such as *Venturia inaequalis*, *Botrytis cinerea* and *Alternaria solani*.

It has now been discovered that certain cycloalkyl and heterocyclic analogues of the compounds of formula A also exhibit fungicidal activity.

According to the invention there is therefore provided a compound of the general formula

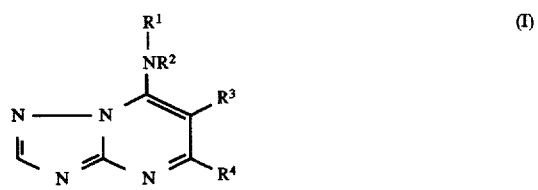
(I)

in which $R^1$ represents an optionally substituted alkyl, alkenyl, alkynyl, alkadienyl, cycloalkyl, bicycloalkyl or heterocyclyl group; $R^2$ represents a hydrogen atom or an alkyl group; or $R^1$ and $R^2$ together with the interjacent nitrogen atom represent an optionally substituted heterocyclic ring; $R^3$ represents an optionally substituted cycloalkyl or heterocyclyl group; and $R^4$ represents a hydrogen or halogen atom or a group —$NR^5R^6$ where $R^5$ represents a hydrogen atom or an amino, alkyl, cycloalkyl or bicycloalkyl group and $R^6$ represents a hydrogen atom or an alkyl group.

When the compounds of this invention contain an alkyl, alkenyl, alkynyl or alkadienyl substituent group, this may be linear or branched and may contain up to 12, preferably up to 6 and especially up to 4, carbon atoms. A cycloalkyl group may contain from 3 to 8, preferably 3 to 6, carbon atoms. A bicycloalkyl group may contain from 4 to 12, preferably 4 to 8, carbon atoms. An aryl group may be any aromatic hydrocarbon group, especially a phenyl or naphthyl group. A heterocyclic ring may be any saturated or unsaturated ring system containing at least one heteroatom, 3- to 6-membered rings being preferred and 5- and 6-membered rings being especially preferred. Nitrogen-, oxygen- and sulphur-containing heterocyclic rings, such as pyridinyl, pyrimidinyl, pyrrolidinyl, furyl, pyranyl, morpholinyl and thienyl, are particularly preferred.

When any of the foregoing substituents are designated as being optionally substituted, the substituent groups which are optionally present may be any one or more of those customarily employed in the development of pesticidal compounds and/or the modification of such compounds to influence their structure/activity, persistence, penetration or other property. Specific examples of such substituents include, for example, halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl, especially furyl, and cycloalkyl, especially cyclopropyl, groups. Typically, 0–3 substituents may be present. When any of the foregoing substituents represents or contains an alkyl substituent group, this may be linear or branched and may contain up to 12, preferably up to 6, and especially up to 4, carbon atoms. When any of the foregoing substituents represents or contains an aryl or cycloalkyl moiety, the aryl or cycloalkyl moiety may itself be substituted by one or more halogen atoms, nitro, cyano, alkyl, haloalkyl, alkoxy or haloalkoxy groups. In the case of cycloalkyl and heterocyclyl groups, optional substituents also include groups which together with two adjacent carbon atoms of the cycloalkyl or heterocyclyl group form a saturated or unsaturated hydrocarbyl ring. In other words, a saturated or unsaturated hydrocarbyl ring may be optionally fused with the cycloalkyl or heterocyclyl group.

It is preferred that $R^1$ represents a $C_{1-12}$ alkyl, $C_{2-6}$ alkenyl, $C_{2-6}$ alkynyl, $C_{4-12}$ alkadienyl, $C_{3-8}$ cycloalkyl or $C_{4-8}$ bicycloalkyl group or a 3- to 6-membered heterocyclic ring, each group or ring being optionally substituted by one or more substituents selected from halogen atoms, nitro, cyano, hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, di-$C_{1-4}$ alkylamino, formyl, $C_{1-4}$ alkoxycarbonyl, carboxyl, phenyl, $C_{1-4}$ haloalkylphenyl, di-$C_{1-4}$ alkoxyphenyl, furyl and dihalo-$C_{3-6}$ cycloalkyl groups or, in the case where $R^1$ represents a $C_{3-8}$ cycloalkyl group or a 3- to 6-membered heterocyclic ring, optionally ortho-fused with a benzene ring.

More preferably, $R^1$ represents a $C_{1-12}$ alkyl, $C_{2-6}$ alkenyl, $C_{2-4}$ alkynyl, $C_{4-8}$ alkadienyl, $C_{3-8}$ cycloalkyl, $C_{4-8}$ bicycloalkyl group or a 3- to 6-membered nitrogen-containing heterocyclic ring, each group or ring being optionally substituted by up to three substituents selected from halogen, especially chlorine, atoms, hydroxyl, $C_{1-4}$ alkyl, especially methyl, $C_{1-4}$ haloalkyl, especially trifluoromethyl, $C_{1-4}$ alkoxy, especially methoxy, $C_{1-4}$ haloalkoxy, especially trifluoromethoxy, phenyl, $C_{1-4}$ haloalkylphenyl, di-$C_{1-4}$alkoxyphenyl, furyl and dihalo-$C_{3-6}$ cycloalkyl groups or, in the case where $R^1$ represents a $C_{3-8}$ cycloalkyl group or a 3- to 6-membered heterocyclic ring, optionally ortho-fused with a benzene ring.

Preferably, $R^2$ represents a hydrogen atom or a $C_{1-4}$ alkyl group.

It is also preferred that $R^3$ represents a $C_{3-8}$ cycloalkyl group or a 3- to 6-membered heterocyclic ring, each group or ring being optionally substituted by one or more substituents selected from halogen atoms; nitro, cyano, hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, di-$C_{1-4}$ alkylamino, formyl, $C_{1-4}$ alkoxycarbonyl, carboxyl, phenyl, phenoxy and benzyloxy groups.

More preferably, $R^3$ represents a $C_{3-6}$ cycloalkyl group or a 5- to 6-membered heterocyclic ring, each group or ring being optionally substituted by up to three substituents selected from halogen atoms, $C_{1-4}$ alkyl, $C_{1-4}$ haloalkyl, $C_{1-4}$ alkoxy and $C_{1-4}$ haloalkoxy groups.

Preferably, $R^4$ represents a hydrogen or halogen atom or a group —$NR^5R^6$ where $R^5$ represents a hydrogen atom or an amino, $C_{1-4}$ alkyl, especially methyl, $C_{3-6}$ cycloalkyl or $C_{4-8}$ bicycloalkyl group and $R^6$ represents a hydrogen atom or a $C_{1-4}$ alkyl, especially methyl, group.

A particularly preferred sub-group of compounds of formula I is that in which $R^1$ represents a propyl, cyclopentyl or bicycloheptyl group; $R^2$ represents a hydrogen atom; $R^3$ represents a thienyl group; and $R^4$ represents a chlorine atom.

The present invention also provides a process for the preparation of a compound of formula I as defined above which comprises a) reacting a compound of the general formula

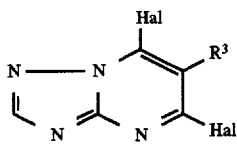 (II)

in which $R^3$ is as defined above and Hal represents a chlorine or bromine atom with a compound of the general formula

 (III)

in which $R^1$ and $R^2$ are as defined above, to produce a compound of formula I in which $R^4$ represents a chlorine or bromine atom;

(b) if desired, reacting the compound of formula I formed in (a) with a fluorinating agent to produce a compound of formula I in which $R^4$ represents a fluorine atom;

(c) if desired, reacting the compound of formula I formed in (a) with a reducing agent to produce a compound of formula I in which $R^4$ represents a hydrogen atom;

(d) if desired, reacting the compound of formula I formed in (a) with a compound of the general formula

 (IV)

in which $R^5$ and $R^6$ are as defined above, to produce a compound of formula I in which $R^4$ represents a group —$NR^5R^6$; and (e) if desired, reacting a compound of formula I formed in (d) in which $R^5$ and $R^6$ both represent a hydrogen atom with diiodomethane in the presence of a diazotising agent to produce a compound of formula I in which $R^4$ represents an iodine atom.

The process of step (a) is conveniently carried out in the presence of a solvent. Suitable solvents include ethers, such as dioxane, diethyl ether and, especially, tetrahydrofuran, halogenated hydrocarbons, such as dichloromethane, and toluene. The reaction is suitably carried out at a temperature in the range from 0° C. to 70° C., the preferred reaction temperature being from 10° C. to 35° C. It is also preferred that the reaction is carried out in the presence of a base. Suitable bases include tertiary amines, such as triethylamine, and inorganic bases, such as potassium carbonate or sodium carbonate. Alternatively, an excess of the compound of formula III may serve as a base.

The process of step (b) is conveniently carried out in the presence of a solvent. Suitable solvents include sulpholane, dimethylformamide or a mixture of acetonitrile and a crown ether. If sulpholane or dimethylformamide is used as solvent, it is advantageous to use toluene as a co-solvent to aid dehydration of the fluorinating agent. The reaction is suitably carried out at a temperature in the range from room temperature (about 15° C.) to the reflux temperature of the reaction mixture, the preferred reaction temperature being from 40° C. to the reflux temperature of the reaction mixture. Suitable fluorinating agents include alkali metal fluorides, especially potassium fluoride, and antimony fluoride.

The reducing agent utilised in step (c) is conveniently a catalytic hydrogenating agent, that is, hydrogen gas used under elevated pressure in the presence of a catalyst. Preferably, the catalyst is palladium on charcoal. It is also preferred that this step is carried out in the presence of a base. Suitable bases include tertiary amines, such as triethylamine, and inorganic bases, such as sodium carbonate or, especially, sodium hydroxide. This step may also be conveniently carried out in the presence of a solvent. Suitable solvents include alcohols, such as methanol. The reaction is suitably carried out at a temperature in the range from 0° C. to 70° C., the preferred reaction temperature being from 10° C. to 35° C.

The process of step (d) is conveniently carried out in the presence of a solvent. Suitable solvents include ethers, such as dioxane, diethyl ether and tetrahydrofuran, halogenated hydrocarbons, such as dichloromethane, and, especially, toluene. The reaction is suitably carried out at a temperature in the range from 20° C. to the reflux temperature of the reaction mixture, the preferred reaction temperature being from 40° C. to the reflux temperature of the reaction mixture. It is also preferred that the reaction is carried out in the presence of a base. Suitable bases include tertiary amines, such as triethylamine, and inorganic bases, such as potassium carbonate or sodium carbonate. Alternatively, an excess of the compound of formula IV may serve as a base.

When $R^1$ represents the same substituent as $R^5$ and $R^2$ represents the same substituent as $R^6$ in the resultant compound of formula I, the compound of formula III will be the same as the compound of formula IV and steps (a) and (d) may therefore be performed as one step by using double the quantity of amine of formula III/IV.

The diazotising agent used in step (e) may be any alkyl ester of nitrous acid, isopentyl nitrite being especially preferred. If an alkyl ester of nitrous acid is used, this may also serve as a co-solvent with the diiodomethane. The reaction is suitably carried out at a temperature from 60° C. to 120° C., the preferred reaction temperature being from 70° C. to 110° C.

Compounds of formula II may be prepared by reacting a compound of the general formula

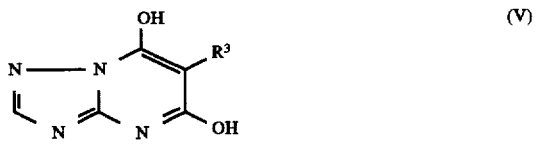 (V)

in which $R^3$ is as defined above, with a chlorinating or brominating agent, such as phosphorus oxychloride or phosphorus oxybromide.

Compounds of formula V can be prepared by reacting 3-amino-1,2,4-triazole with an appropriate malonic acid ester under alkaline conditions according to the method of Y. Makisumi, Chem. Pharm. Bull., 9, 801, (1961).

Compounds of formula III and IV are known compounds or can be prepared by processes analogous to known processes.

The compounds of general formula I have been found to have fungicidal activity. Accordingly, the invention further provides a fungicidal composition which comprises a carrier and, as active ingredient, a compound of formula I as defined above. A method of making such a composition is also provided which comprises bringing a compound of formula I as defined above into association with at least one carrier. Such a composition may contain a single compound or a mixture of several compounds of the present invention.

A composition according to the invention preferably contains from 0.5 to 95% by weight of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating fungicidal compositions may be used.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinated mineral waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example, kerosine and light mineral oils; chlorinated hydrocarbons, for example carbon tetrachloride, perchloroethylene and trichloroethane. Mixtures of different liquids are often suitable.

Fungicidal compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and may be diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–75% w active ingredient and 0–10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 1–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise' like consistency.

The composition of the invention may also contain other ingredients, for example other compounds possessing herbicidal, insecticidal or fungicidal properties.

Of particular interest in enhancing the duration of the protective activity of the compounds of this invention is the use of a carrier which will provide a slow release of the fungicidal compounds into the environment of the plant which is to be protected. Such slow-release formulations could, for example, be inserted in the soil adjacent to the roots of a vine plant, or could include an adhesive component enabling them to be applied directly to the stem of a vine plant.

The invention still further provides the use as a fungicide of a compound of the general formula I as defined above or a composition as defined above, and a method for combating fungus at a locus, which comprises treating the locus, which may be for example plants subject to or subjected to fungal attack, seeds of such plants or the medium in which such plants are growing or are to be grown, with such a compound or composition.

The present invention is of wide applicability in the protection of crop plants against fungal attack. Typical crops which may be protected include vines, grain crops such as wheat and barley, apples and tomatoes. The duration of protection is normally dependent on the individual compound selected, and also a variety of external factors, such as climate, whose impact is normally mitigated by the use of a suitable formulation.

The invention is further illustrated by the following examples.

EXAMPLE 1

Preparation of 5-chloro-6-thien-3-yl-7-cyclopentylamino-1,2,4-triazolo[1,5-a]pyrimidine
($R^1$-cyclopentyl; $R^2$—H; $R^3$-thien-3-yl; $R^4$—Cl)

5,7-Dichloro-6-thien-3-yl-1,2,4-triazolo[1,5-a] pyrimidine (0.54 g, 0.002 mol) was dissolved in tetrahydrofuran (20 ml). A mixture of cyclopentylamine (0.2 g, 0.002 mol), tetrahydrofuran (2 ml) and triethylamine (0.25 g, 0.002 mol) was then added with stirring and the stirring continued for a further hour after the addition was complete. The solvent was then distilled off in vacuo and the residue treated with ethyl acetate and water (50 ml each). The organic phase was separated, dried with sodium sulphate, filtered and the solvent removed in vacuo. The residue was purified by chromatography on silica gel using 8:2 ethyl acetate: petroleum ether (300 ml) as eluant to give 0.45 g 5-chloro-6-thien-3yl-7-cyclopentylamino-1,2,4-triazolo[1, 5-a]-pyrimidine as colourless crystals, m.pt. 78° C. Yield: 71% of theoretical.

EXAMPLES 2 and 3

By processes similar to those described in Example 1 above, further compounds were prepared as detailed in Table I below. In this table the compounds are identified by reference to formula I.

TABLE I

| Ex. No. | $R^1$ | $R^2$ | $R^3$ | $R^4$ | M.pt (°C.) |
|---|---|---|---|---|---|
| 2 | —CH(CH$_3$)$_2$ | H | thien-3-yl | Cl | 144 |
| 3 | bicyclo[2.2.1]hept-2-yl | " | " | " | 156 |

EXAMPLE 4

The fungicidal activity of compounds of the invention was investigated by means of the following tests.

(a) Antisporulant activity against vine downy mildew (Plasmopara viticola; PVA)

The test is a direct antisporulant one using a foliar spray. The lower surface of leaves of vine plants (cv. Cabernet Sauvignon), approximately 8 cm high, are inoculated with an aqueous suspension containing 5×10$^4$ zoosporangia/ml. The inoculated plants are kept for 24 hours at 21° C. in a high humidity cabinet, then for 24 hours in a glasshouse at 20° C. and 40% relative humidity. Infected leaves are sprayed on their lower surfaces with a solution of the test compound in 1:1 water/acetone containing 0.04% "TWEEN 20" (Trade Mark; a polyoxyethylene sorbitan ester surfactant). Plants are sprayed using a track sprayer equipped with 2 air-atomising nozzles. The concentration of the compound is 600 ppm and the spray volume is 750 l/ha. After drying, the plants are returned to the glasshouse at 20° C. and 40% relative humidity for 96 hours and are then transferred to the high humidity cabinet for 24 hours to induce sporulation. Assessment is based on the percentage of the leaf area covered by sporulation compared with that on control leaves.

(b) Direct protectant activity against tomato late blight (Phytophthora infestans; PIP)

The test is a direct protectant one using a foliar spray. Tomato plants with two expanded leaves (cv. First in the Field) are sprayed with the test compound at a dosage of 600 ppm as described under (a). After drying, the plants are kept for 24 hours in a glasshouse at 20° C. and 40% relative humidity. The upper surfaces of the leaves are then inoculated with an aqueous suspension containing 2×10$^5$ zoosporangia/ml. The inoculated plants are kept for 24 hours at 18° C. in a high humidity cabinet and then for 5 days in a growth chamber at 15° C. and 80% relative humidity with 14 hours light/day. The assessment is based on the percentage of diseased leaf area compared with that on control leaves.

(c) Activity against tomato early blight (Alternaria solani; AS)

The test is a direct prophylactic one using a foliar spray. Tomato seedlings (cv Outdoor Girl), at the stage at which the second leaf is expanded, are sprayed with the test compound at a dosage of 600 ppm as described under (a). After drying, the plants are kept for 24 hours in a glasshouse at 20° C. and 40% relative humidity followed by inoculation of the leaf upper surfaces with an aqueous suspension of A. solani conidia containing 1×10$^4$ conidia/ml. After 4 days in a high humidity cabinet at 21° C., disease is assessed based on the percentage of leaf surface area covered by lesions when compared with control plants.

(d) Direct protectant activity against broad bean grey mould (Botrytis cinerea; BCB)

The test is a direct protectant one using a foliar spray. Broad bean plants (cv The Sutton) with two leaf pairs are sprayed with the test compound at a dosage of 600 ppm as described under (a). After drying, the plants are kept for 24 hours in a glasshouse at 20° C. and 40% relative humidity. The upper surface of the leaves are then inoculated with an aqueous suspension containing 1×10$^6$ conidia/ml. Plants are kept for 4 days at 22° C. in a high humidity cabinet. The assessment is based on the percentage of diseased leaf area compared with that on control leaves.

(e) Activity against wheat eyespot in-vitro (Pseudocercosporella herpotrichoides; PHI)

This test measures the in vitro activity of compounds against the fungus causing wheat eyespot. The test compound is dissolved or suspended in acetone and is added into 4 ml aliquots of half strength Potato Dextrose Broth dispensed in 25-compartment petri dishes to give a final concentration of 30 ppm test compound and 0.825% acetone. The fungal inoculum consists of mycelial fragments of P. herpotrichoides grown in half strength Potato Dextrose Broth in shaken flasks and added to the broth to provide 5×10$^4$ mycelial fragments/ml broth. Petri dishes are incubated at 20° C. for 10 days until the assessment of mycelial growth.

(f) Activity against Rhizoctonia in-vitro (Rhizoctonia solani RSI)

The test measures the in-vitro activity of compounds against Rhizoctonia solani that causes stem and root rots. The test compound is dissolved or suspended in acetone and added into 4 ml aliquots of half strength Potato Dextrose Broth dispensed in 25-compartment petri dishes to give a final concentration of 30 ppm compound and 0.825% acetone. The fungal inoculum consists of mycelial fragments of R. solani grown in half strength Potato Dextrose Broth in shaken culture flasks and added to the broth to provide 5×10⁴ fragments/ml broth. Petri dishes are incubated at 20° C. for 10 days until the assessment of mycelial growth.

(g) Activity against apple scab in-vitro (Venturia inaequalis; VII)

This test measures the in-vitro activity of compounds against *Venturia inaequalis* that causes apple scab. The test compound is dissolved or suspended in acetone and added into 4ml aliquots of half strength Potato Dextrose Broth dispensed in 25-compartment petri dishes to give a final concentration of 30 ppm compound and 0.825% acetone. The fungal inoculum consists of mycelial fragments and spores of *V. inaequalis* grown on malt agar and added to the broth to provide 5×10⁴ propagules/ml broth. Petri dishes are incubated at 20° C. for 10 days until the assessment of mycelial growth.

The extent of disease control in all the above tests is expressed as a rating compared with either an untreated control or a diluent-sprayed-control, according to the criteria:

0=less than 50% disease control
1=50–80% disease control
2=greater than 80% disease control The results of these tests are set out in Table II below:

TABLE V

| Example | Fungicidal Activity | | | | | | |
|---|---|---|---|---|---|---|---|
| No. | PVA | PIP | AS | BCB | PHI | RSI | VII |
| 1 | 2 |  | 2 | 2 | 1 | 2 | 2 |
| 2 | 2 | 1 |  | 1 |  | 1 | 2 |
| 3 | 2 |  | 2 |  | 1 | 1 | 2 |

I claim:

1. A compound of the formula:

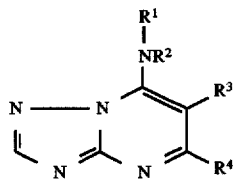

(I)

in which $R^1$ represents $C_{1-12}$ alkyl, $C_{2-6}$ alkenyl, $C_{2-6}$ alkynyl, $C_{4-12}$ alkadienyl, $C_{3-8}$ cycloalkyl or bicycloheptyl or thienyl, each group or ring being optionally substituted by a substituent selected from halogen atoms, nitro, cyano, hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, di-$C_{1-4}$ alkylamino, formyl, $C_{1-4}$ alkoxycarbonyl, carboxyl, phenyl, $C_{1-4}$ haloalkylphenyl, di-$C_{1-4}$ alkoxyphenyl, furyl and dihalo-$C_{3-6}$ cycloalkyl groups or, wherein $R^1$ represents a $C_{3-8}$ cycloalkyl group or thienyl;

$R^2$ represents hydrogen or a $C_{1-4}$ alkyl group;

$R^3$ represents a $C_{3-8}$ cycloalkyl group or thienyl, each group or ring being optionally substituted by a substituent selected from halogen, nitro, cyano, hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, di-$C_{1-4}$ alkylamino, formyl, $C_{1-4}$ alkoxycarbonyl, carboxyl, phenyl, phenoxy and benzyloxy groups; and $R^4$ represents a hydrogen or halogen atom or a group —$NR^5R^6$ where $R^5$ represents a hydrogen atom or an amino, $C_{1-4}$ alkyl, $C_{3-6}$ cycloalkyl, or bicycloheptyl group and $R^6$ represents a hydrogen atom or a $C_{1-4}$ alkyl group.

2. A compound according to claim 1, wherein $R^1$ is propyl, cyclopentyl or bicycloheptyl, $R^2$ is hydrogen, $R^3$ is thienyl and $R^4$ is chlorine.

3. A compound according to claim 1 wherein $R^1$ is cyclopentyl, $R^2$ is hydrogen, $R^3$ is thien-3-yl and $R^4$ is Cl.

4. A compound according to claim 1 wherein $R^1$ is cyclopentyl, $R^2$ is hydrogen, $R^3$ is cyclopentyl and $R^4$ is Cl.

5. A compound according to claim 1 wherein $R^1$ is cyclopentyl, $R^2$ is hydrogen, and $R^4$ is halogen.

6. A compound according to claim 1 wherein $R^1$ is —$CH(CH_3)_2$, $R^2$ is hydrogen, $R^3$ is thien-3-yl and $R^4$ is Cl.

7. A compound according to claim 1 wherein $R^1$ is bicylo[2.2.1]hept-2-yl, $R^2$ is hydrogen, $R^3$ is thien-3-yl, and $R^4$ is Cl.

8. A fungicidal composition which comprises a carrier and, as active ingredient, a fungicidally effective amount of a compound of formula I as defined in claim 1.

9. A fungicidal composition according to claim 8 which comprises two carriers, at least one of which is a surface active agent.

10. A method of combating fungus at a locus, which comprises treating the locus with a fungicidally effective amount of a compound of formula I as defined in claim 1.

11. A method of combating fungus at a locus according to claim 10, wherein said locus comprises plants subject to or subjected to fungal attack, seeds of such plants or the medium in which such plants are growing or are to be grown.

12. A method of combating fungus at a locus, which comprises treating the locus with a fungicidally effective amount of a composition as defined in claim 8.

13. A compound according to claim 1 wherein $R^1$ is $C_{3-8}$ cycloalkyl.

14. A compound according to claim 13 wherein $R^4$ is hydrogen or halogen.

15. A compound according to claim 14 wherein $R^4$ is chlorine.

16. A compound according to claim 13 wherein $R^2$ is hydrogen.

* * * * *